(12) United States Patent
Popovsky et al.

(10) Patent No.: US 8,546,640 B2
(45) Date of Patent: Oct. 1, 2013

(54) INFUSED SPONGE DELIVERY SYSTEM

(75) Inventors: Michael Popovsky, Beverly Hills, CA (US); Yelena Popovsky, Beverly Hills, CA (US); Paul Thau, Berkeley Heights, NJ (US)

(73) Assignee: Evriholder Products, LLC, Anaheim, CA (US)

( * ) Notice: Subject to any disclaimer, the term of this patent is extended or adjusted under 35 U.S.C. 154(b) by 463 days.

(21) Appl. No.: 12/308,108

(22) PCT Filed: Jun. 8, 2007

(86) PCT No.: PCT/US2007/013478
§ 371 (c)(1),
(2), (4) Date: Dec. 8, 2008

(87) PCT Pub. No.: WO2007/146103
PCT Pub. Date: Dec. 21, 2007

(65) Prior Publication Data
US 2009/0285875 A1 Nov. 19, 2009

Related U.S. Application Data

(60) Provisional application No. 60/812,578, filed on Jun. 8, 2006.

(51) Int. Cl.
*A61F 13/15* (2006.01)
*A61F 13/00* (2006.01)
*A61L 9/01* (2006.01)

(52) U.S. Cl.
USPC . 604/367; 604/359; 604/385.15; 604/385.19; 424/443; 424/761

(58) Field of Classification Search
USPC ....... 604/367, 359, 385.15, 385.19; 424/443, 424/76.1, 76.4
See application file for complete search history.

(56) References Cited

U.S. PATENT DOCUMENTS

| | | | | |
|---|---|---|---|---|
| 5,100,879 A | * | 3/1992 | Ueno et al. | 514/59 |
| 6,086,903 A | * | 7/2000 | Trinh et al. | 424/401 |
| 6,153,209 A | * | 11/2000 | Vega et al. | 424/404 |
| 6,190,677 B1 | | 2/2001 | Remy | |
| 6,296,880 B1 | | 10/2001 | Murad | |
| 6,626,961 B1 | * | 9/2003 | Everhart et al. | 8/115.51 |
| 2004/0047905 A1 | * | 3/2004 | Padlo | 424/465 |
| 2005/0000046 A1 | | 1/2005 | Popovsky | |

FOREIGN PATENT DOCUMENTS

| | | |
|---|---|---|
| WO | 2005/105032 A | 11/2005 |
| WO | 2005/108383 A | 11/2005 |

* cited by examiner

*Primary Examiner* — Jacqueline F. Stephens
(74) *Attorney, Agent, or Firm* — Louis C. Paul

(57) ABSTRACT

A method for delivering active ingredients to a wet substrate from a flexible, three-dimensional, water-absorbent substrate material comprised of a web of substantially water-insoluble fibers into which is infused a solid anhydrous composition having a melting point of from about 45° C. to about 55° C. said anhydrous composition comprising (i) at least one surfactant selected from the group consisting of cationic quaternary surfactants, anionic surfactants or nonionic surfactants or one multi-lamellar liquid crystal emulsifier system, (ii) at least one fatty alcohol, (iii) at least one emollient selected from the group consisting of cosmetically-acceptable oils, esters and liquid triglycerides, (iv) at least one active ingredient and (v) optionally, a solid cleansing agent having a melting point from about 50° C. to about 70° C. Preferred active ingredients are skincare and haircare actives, including emollients, humectants, conditioning agents, sunscreens and sunblocks, and artificial tanning agents.

11 Claims, No Drawings

INFUSED SPONGE DELIVERY SYSTEM

CROSS-REFERENCE TO RELATED APPLICATIONS

This application claims priority to U.S. Provisional Application Ser. No. 60/812,578 filed on 8 Jun. 2006 and entitled "Applicator Tool Having Sponge with Detergent". The disclosure of this application is incorporated herein by reference.

This is a continuation-in-part of PCT/US2004/021435 filed on 2 Jul. 2004 and entitled "Improved Cleansing Pad", now national phase U.S. application Ser. No. 10/562,311 and published as US Patent Application Publication No. 2006/0282966 ("the '435 PCT Application"). The '435 PCT Application is a continuation-in-part of U.S. application Ser. No. 10/696,069 filed on 28 Oct. 2003 and entitled "Cleansing Pad" ("the '069 US Application"). Both the '435 PCT Application and the '069 US Application claim priority to U.S. Provisional Application Ser. No. 60/484,786 filed on 3 Jul. 2003, and entitled "Soap and Wash Sponge." The present application thus claims priority to PCT/US2004/021435, U.S. application Ser. No. 10/696,069 and U.S. Provisional Application Ser. No. 60/484,786. The disclosures of each of PCT/US2004/021435, U.S. application Ser. No. 10/696,069, and U.S. Provisional Application Ser. No. 60/484,786 are incorporated herein by reference in their entirety.

FIELD OF INVENTION

The present invention relates to infused sponges useful for delivering conditioning, sun-protecting and other active ingredients to the skin and hair and other substrates.

STATEMENT OF FEDERALLY-SPONSORED RESEARCH

Not Applicable.

BACKGROUND OF THE INVENTION

The use of sponge-like materials to apply conditioning and other cosmetic and skincare ingredients is known in the art. In some prior art products, a sponge is infused with a predetermined quantity of a cosmetic product. For example, U.S. Pat. No. 6,945,253 describes a single-use cosmetic applicator sponge infused with moisturizer, cleanser, toner, make-up and tanning mousse. (To the extent pertinent, granted US patents and published US patent applications disclosed in this application are incorporated herein by reference in their entirety.) ULTA sells vitamin E infused sponges for use in applying makeup. See the following webpage accessed 29 May 2007: http://www.ulta.com/control/product/~product_id=8011258. In another prior art product, Advanced Solutions MicroDermabrasion System from Neutrogena, a cosmetic composition is applied to a sponge and then to the skin or directly to the skin. An exfoliating cream containing antioxidants and vitamins is applied to a sponge head applicator and dotted onto the cheeks, chin and forehead. The applicator is used to gently massage the cream into the facial areas. There are, however, drawbacks in prior art infused sponges, including limitations on the number of uses and/or the ability to deliver active materials in a manner that provides substantive deposition on the desired substrate (e.g., skin or hair). These limitations are met by the articles of the present invention.

The use of quaternium cationic surfactants, more commonly referred to as "quats," as conditioning agents in skincare and haircare compositions is well-known. Quats are ammonium salts in which hydrogen molecules are replaced by alkyl groups, at least one of which is a hydrocarbon chain, typically from 12 to 22 carbons in length, with the remaining alkyl groups being methyl. The counter anion in many quats is typically chloride but may also be another halide or a sulfate. See, e.g., *Cosmetics & Toiletries*, Vol. 110, No. 8, pp. 43-46 (1995.) Among the numerous quats used in personal care formulations are behentrimonium methosulfate (having three methyl groups and one behenyl group) distearyldimonium chloride (having two stearyl and two methyl groups) and steapyrium chloride.

The water-soluble and water-insoluble groups on surfactants are often referred to, respectively, as "head" and "tail". The ability of quats to condition is attributable to the hydrophobic nature of the long hydrocarbon tail and the Cationic charge on the polar head. In an aqueous environment, quats dissociate into their ionic components. The electrostatic attraction between the cationic polar head and the anionic charge on skin and hair proteins, in combination with the lipophilic properties of the hydrocarbon tail, enable quats to confer substantivity and inhibit rinse-off.

U.S. Pat. No. 6,709,663 teaches a system for topical delivery of active ingredients from a multi-lamellar oil-in-water emulsion system comprised of a quaternary amine salt (i.e., behentrimonium methosulfate) at a use concentration of from 0.5% by weight of the total composition to about 5% by weight of the total composition and a fatty alcohol secondary emulsifier (i.e., cetearyl alcohol) where the fatty alcohol is present at a concentration of from 1.5 times to four times the amount of the behentrimonium methosulfate. (Unless otherwise indicated, percentages are based on the weight percentage of an ingredient relative to the weight of the entire composition.)

U.S. Pat. No. 6,024,951 teaches the combination of a fatty alcohol (at a concentration of from about 0.75% to about 22.5%) and a behenylquaternary surfactant (at a concentration of from about 0.25% to about 7.5%) in a shaving lotion emulsion, where water comprises from about 40% to about 90% of the emulsion.

U.S. Pat. Nos. 5,633,403 and 5,601,811 teach personal care emulsions containing substantive water-soluble cationic UV-absorbing compounds (specifically cinnamido amine cationic quaternary salts). Among the examples taught in these patents is a hair conditioner formulation comprising behentrimonium methosulfate and a fatty alcohol (stearyl alcohol).

U.S. Pat. No. 5,696,069 teaches detergent, personal cleansing and cosmetic compositions having (i) an acyl taurate surfactant, (ii) a quaternium cation surfactant, (iii) low Hydrophile-Lipophile Balance ("HLB") nonionic surfactants, and (iv) water. Among the disclosed cationic quats is distearyldimonium chloride. The low HLB nonionic surfactants are taught to be in the form of a solution or dispersion. The compositions infused in the personal care articles of the present invention do not contain acyl taurate surfactants.

U.S. Pat. Nos. 6,730,292 and 6,849,252 teach a rinse-off hair conditioner gel where the gel matrix is comprised of a cationic surfactant (preferably dialkylamido ethyl hydroxyethylmonium salt, dialkylamidoethyl dimonium salt, dialkyloyl ethyl hydroxyethylmonium salt or dialkyloyl ethyldimonium salt), a solid fatty compound (including stearyl and cetyl alcohols) and water. The ratio of the cationic surfactant to fatty solid is taught to be preferably from about 1:2 to about 1:10, and more preferably form about 1:3 to 1:5.

U.S. Pat. No. 5,229,104 teaches artificial tanning emulsion compositions containing positively-charged, concentric, lipid bilayer vesicles encapsulating an aqueous dihydroxyacetone solution. The vesicles are taught to be comprised of a polyoxyalkylene alkyl ethers (including Steareth-2), a sterol (cholesterol) and quaternary ammonium compounds (including distearyldimethyl ammonium chloride and steapyrium chloride). The use of number of emulsifiers well-known to those of skill in the art, including Steareth-20, is disclosed.

Unlike the emulsions systems taught in the prior art patents discussed in the preceding paragraphs, the solid compositions infused into the personal care articles of the present invention are anhydrous.

US Patent Application Publication No. 2003/0108502 is directed to anhydrous hair conditioning compositions that can be applied to wet hair and/or wet skin to mix with water remaining on the hair and/or skin. More particularly, the disclosed anhydrous compositions relate to hair conditioners comprised of (i) a hydrophobic polyol (polypropylene glycol having a molecular weight of from about 200 to about 100,000), (ii) a hydrophilic polyol (propylene glycol, butylene glycol, hexylene glycol, glycerin, diglycerin, polyethylene glycol, and mixtures thereof), (iii) an oily conditioning agent, which is taught to include $C_{14}$-$C_{32}$ fatty alcohols and silicones and (iv) a cationic surfactant. Preferred cationic surfactants are taught to include behenyl trimethyl ammonium chloride and distearyl dimethyl ammonium chloride. The '502 application Publication teaches the difficulty of obtaining expected conditioning efficacy from cosmetic compositions comprising oily conditioning components and a hydrophilic polyol carrier and claims that the pairing of specific hydrophobic and hydrophilic polyols provides better deposition and thus product efficacy in terms of conditioning benefits. The solid anhydrous compositions infused into the personal care articles of the present invention provide excellent conditioning as well as the ability to deliver desired active ingredients without the use of the hydrophobic and hydrophilic polyol pairings disclosed in the '502 application Publication.

In addition to haircare applications, steapyrium choloride has been used in skincare formulations for over forty years. Among the first such uses was Mennen's Baby Magic Lotion, which contained Emcol-E 607S at a concentration of below 1.00%.

U.S. Pat. Nos. 6,923,975 and 7,192,598 describe methods of enhancing moisture or reducing drying using a "wet skin" rinse-off treatment composition comprising an aqueous phase and a structured oil phase, the latter comprising a skin compatible oil (ester oils, hydrocarbon oils, and silicone oils) that is liquid below 35° C. and a structurant that forms a stable network of finely divided solids at a temperature below 35° C.

The use of cationic conditioning agents as part of a delivery system matrix is known in the art. U.S. Pat. No. 7,208,460 describes the use of hydrophobic, positively-charged, solid nanospheres to deliver encapsulated active ingredients from soap bars. More particularly, a high cationic charge density is taught to be created on the surface of the disclosed nanospheres by incorporating a cationic conditioning agent and/or cationic charge booster into the solid hydrophobic matrix of the nanospheres.

U.S. Pat. Nos. 6,998,113, 7,001,592, 7,025,952 and 7,037,513 teach bodywash compositions containing sunscreen actives encapsulated in sol-gel microcapsules made of silica or modified silica, and a cationic polymer, preferably polyquaternium. The disclosed compositions are claimed to deposit sunscreens on the skin or hair after washing with the bodywash.

U.S. Pat. No. 6,362,146 teaches a personal washing composition containing (i) a surfactant, anionic, nonionic, zwitterionic or cationic, as well as soaps and mixtures of surfactants and/or soaps, (ii) a polymeric deposition aid (defined as a polymer with a cationic charge) and (iii) a sunscreen active encapsulated in a natural or synthetic wax capsule.

U.S. Pat. No. 4,969,226 teaches the use in a sponge of hydrophilic urethane polymers previously sold under the tradename Hypol by W. R. Grace & Co. The Hypol polymers are isocyanate-capped polyoxyethylene polyols that readily react with water and are further described in U.S. Pat. No. 3,889,417. These products were, however, difficult to scale-up commercially.

Multi-lamellar liquid crystal emulsion systems are emulsifier systems which form lamellar liquid crystals that mimic the multi-lamellar lipid structure of the stratum corneum and are known to those of skill in the art. They include Montanov® 68 (INCI: Cetearyl Alcohol and Cetearyl Glucoside) from Seppic Inc., and Crystalcast® (INCI: Cetearyl Alcohol, Sucrose Distearate and Sucrose Monostearate) from MMP, Inc. The latter is described in PCT/US2005/013023.

The use of solid fatty alcohols to promote lamellar phase formation in oil-in-water emulsions is known in the art. See, e.g., New Paradigm Technologies "Biobase™S: Product Information," p. 1 (Undated) (combination glyceryl stearate, cetearyl alcohol and sodium stearoyl lactylate); International Specialty Products, "Prolipid™ 141 For Skin Care," pg. 2 (April 1999) (use of behenyl, lauryl, myristyl and cetyl alcohols to aid in formation of lamellar phase in an emulsifier system also consisting of glyceryl stearate, stearic acid, palmitic acid and lecithin); Seppic, Inc., "Montanov: Emulsifiers in Harmony with Nature", p. 1 (July 2000) (combination of solid fatty alcohols and glucosides).

SUMMARY OF THE INVENTION

The present invention is directed to sponges and similar flexible, three-dimensional, water-absorbent substrate materials infused with conditioning/moisturizing and/or other active ingredients for application to a wet substrate, preferably wet skin or wet hair (i.e., after washing). The solid anhydrous composition infused into the sponge is mixed with water remaining on the substrate thereby forming an emulsion that is substantive to and remains on the substrate for a period of time sufficient to meet the desired consumer need (e.g., moisturization, protection from ultraviolet radiation, imparting of an artificial tan).

One aspect of the present invention is directed to a method for delivering active ingredients to wet skin or wet hair from a personal care article comprising contacting the wet hair or wet skin with a flexible, three-dimensional, water-absorbent substrate material into which is infused a solid anhydrous composition having a melting point of from about 45° C. to about 55° C. and comprised of (i) at least one surfactant selected from the group consisting of cationic quaternary surfactants, anionic surfactants and non-ionic surfactants, (ii) at least one emollient selected from the group consisting of cosmetically-acceptable oils, esters and liquid triglycerides, (iii) at least one, preferably two, fatty alcohol(s), (iv) at least one skincare or haircare active ingredient and (v) optionally, a solid cleansing agent having a melting point from about 50° C. to about 70° C.

Another aspect of the present invention is directed to a method for delivering active ingredients to wet skin or wet hair from a personal care article comprising contacting the wet hair or wet skin with a flexible, three-dimensional, water-absorbent substrate material into which is infused a different solid anhydrous composition, one having a melting point of from about 45° C. to about 55° C. and comprised of (i) at least one multi-lamellar liquid crystal emulsifier system, (ii) at least one, preferably two, nonionic surfactant(s), (iii) at least one, preferably two, fatty alcohol(s), (iv) at least one emollient selected from the group consisting of cosmetically-acceptable oils, esters and liquid triglycerides, (v) at least one skincare active ingredient, and (vi) optionally, a pourable soap.

DETAILED DESCRIPTION OF THE INVENTION

One aspect of the present invention is directed to a method for delivering active ingredients to wet skin or wet hair from a personal care article comprising contacting the wet hair or wet skin with a flexible, three-dimensional, water-absorbent substrate material comprised of a web of substantially water-insoluble fibers into which is infused a solid anhydrous composition having a melting point of from about 45° C. to about 55° C. and comprised of (a) at least one surfactant selected from the group consisting of cationic quaternary surfactants, anionic surfactants and non-ionic surfactants or at least one multilamellar liquid crystal emulsifier system, (b) at least one fatty alcohol, preferably two, (c) at least one emollient selected from the group consisting of cosmetically-acceptable oils, esters and liquid triglycerides, (d) at least one skincare or haircare active ingredient and (e) optionally, a solid cleansing agent having a melting point from about 50° C. to about 70° C.

Flexible, Three-Dimensional, Water-Absorbent Substrate

Flexible, three-dimensional water-absorbent substrate materials suitable for use in the personal care article of the present invention are well-known to those of skill in the art and are commercially-available from a number of suppliers. Water-absorbent, substrate materials may be natural, synthetic or both. They may comprise woven materials, non-woven materials, polyurethanes (both open and closed cell), sponges or mixtures of the above. For purposes of the present application, substrate materials suitable for use in the cleansing article of the present invention are also referred to as "sponge-like materials."

Suitable natural fibers include, but are not limited to, cellulosic fibers, such as wood pulp fibers and cotton. Suitable synthetic fibers include fibers commonly used in textiles, including, but not limited to, polyester, polypropylene, polyethylene and polyether and combinations thereof. Included within the term "synthetic fibers" are those obtained primarily from natural materials that have been further modified, either chemically, physically, or both. For example, rayon, a chemically-modified natural cellulosic fiber, may also be used in the present invention.

In one preferred embodiment of the present invention, the water-absorbent substrate is a non-woven high loft batting material which is sponge-like in structure and appearance. These materials, including methods of preparation thereof, are further described in US Patent Application Publication No. 2005/0125877.

Other materials suitable for use as water-absorbent, substrate materials in the present invention, include non-woven materials and polymeric sponges as described in U.S. Pat. Nos. 6,984,617 and 6,547,063.

As will be appreciated by persons of skill in the art, compressibility (resistance), density and porosity affect absorption by the flexible, three-dimensional, water-absorbent substrate of the at least one skincare or haircare active and the optional solid cleansing agent. These parameters, in turn, will affect the size and shape of the personal care article. Resistance can range from about 2.5 kPa to about 3.5 kPa (1.5 to 3 psi). Density can range from about 30 kg/m$^3$ to about 35 kg/m$^3$. The substrate may be comprised of both reticulated (open) and non-reticulated (closed) pores, the former being preferred. Pore size can range from about 1 to 40 pores per cm$^2$.

Solid Anhydrous Composition

A first aspect of the present invention is directed to delivery of a solid anhydrous composition infused into a sponge-like material onto a wet substrate where the solid anhydrous composition has a melting point of from about 45° C. to about 55° C. and is comprised of at least one cationic quaternary surfactant.

In one preferred embodiment of this aspect of the invention, the at least one cationic quaternary surfactant is behentrimonium methosulfate, a quaternary ammonium salt having the empirical formula $C_{25}H_{54}N.CH_3O_4S$ and conforming to the structure:

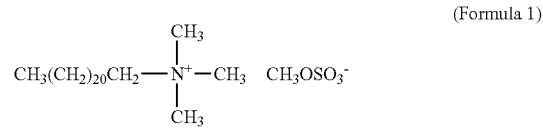

(Formula 1)

It is available from multiple suppliers, including as a 50% active blend with cetearyl alcohol under the trade name Incroquat Behenyl TMS-50 from Croda, Inc. In the present invention, behentrimonium methosulfate is used on an active basis at a concentration from about 1.5% to about 6%.

In another preferred embodiment of this aspect of the invention, the at least one cationic quaternary surfactant is distearyldimonium chloride, a quaternary ammonium salt having the empirical formula $C_{38}H_{80}N.Cl$ and conforming to the structure:

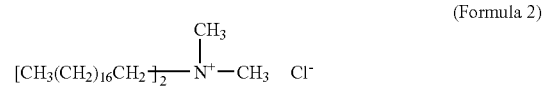

(Formula 2)

It is commercially-available from a number of suppliers, including as Varisoft TA100 from Degussa. In the present invention, distearyldimonium chloride is used at a concentration from about 3% to about 12%.

In yet another preferred embodiment of this aspect of the invention, the at least one cationic quaternary surfactant is steapyrium chloride, a quaternary ammonium salt having the empirical formula $C_{27}H_{47}N_2O_3.Cl$ and conforming to the structure:

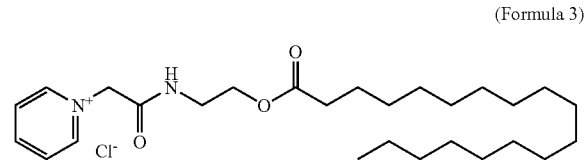 [SMILES: CCCCCCCCCCCCCCCCCC(=O)OCCNC(=O)C[n+]1ccccc1 ; [Cl-]]

(Formula 3)

It is commercially-available from multiple suppliers, including as Emcol 607S from Witco. In the present invention, steapyrium chloride is used on an active basis at a concentration from about 0.5% to about 4%.

Other cationic quaternary surfactants may be used in the solid anhydrous compositions of this aspect of the present invention. These include alkylamido quats, imidazoline quats and polymeric quats as described in Anthony J. O'Lenick, Jr.

*Surfactants: Strategic Personal Care Ingredients* (Allured Publishing, 2005), the disclosure of which is incorporated herein by reference. Other suitable cationic quaternary surfactants are described in McCutcheon's *Detergents and Emulsifiers* (1986), the disclosure of which is also incorporated herein by reference.

One preferred alkylamido quat according to this aspect of the invention is cocamidopropyl PG-dimonium chloride phosphate, commercially available as Monaquat PTC from Uniqema, conforming to the structure:

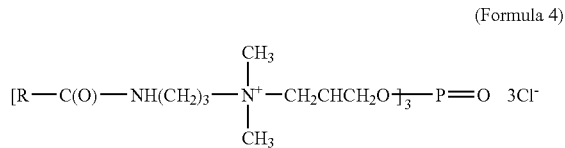

(Formula 4)

Another preferred alkylamido quat according to this aspect of the invention is lauramidopropyl PG-dimonium chloride phosphate, commercially available as Monaquat PTL from Uniqema, conforming to the structure:

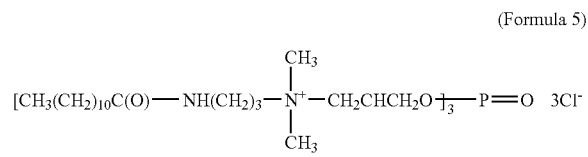

(Formula 5)

Cocamidopropyl- and lauramidopropyl PG-dimonium chloride phosphates are preferably used in the solid anhydrous compositions of the present invention at a concentration of from about 0.5% to about 2.5%.

A preferred imidazoline quaternary is behenyl hydroxyethyl imidazoline which can be used in the solid anhydrous compositions of the present invention at a concentration of from about 0.5% to about 2.5%.

A preferred polymeric quaternary compound is Polyquaternium 10 available under the tradename Polymer JR-125 from Amerchol which can be used in the solid anhydrous compositions of the present invention at a concentration of from about 0.5% to about 3%. In this embodiment, Polyquaternium 10 is used in combination with at least one nonionic surfactant.

A second aspect of the present invention is directed to delivery of a solid anhydrous composition infused into a sponge-like material onto a wet substrate where the solid anhydrous composition has a melting point of from about 45° C. to about 55° C. and is comprised of at least one multilamellar liquid crystal emulsifier system.

A preferred multilamellar liquid crystal emulsifier system is Crystalcast® from MMP Inc., a mixture of at least one solid fatty alcohol having a melting point of at least about 45° C. and two sucrose esters—the first having an HLB of from about 10 to about 16, the second having an HLB of from about 2 to about 8. This multilamellar liquid crystal emulsifier system is described in PCT/US2005/013023.

In preferred embodiments of the first aspect of the present invention, the at least one non-ionic surfactant is an alkyl polyalkylene glycol ether conforming to the formula:

(Formula 6)

where R is $C_6$-$C_{22}$ alkyl and n is an integer ranging from 1 to 40, preferably from 1 to 20. More particularly, alkyl polyalkylene glycol ethers are obtained by acid-catalyzed or preferably base-catalyzed addition of ethylene oxide and/or propylene oxide onto primary alcohols.

Preferred alkyl polyalkylene glycol ethers suitable for use in the anhydrous compositions of the present invention are adducts of, on average, 1 to 20 moles, of ethylene oxide and/or propylene oxide with 1 mole of the following alcohols: caproic alcohol, caprylic alcohol, 2-ethylhexyl alcohol, capric alcohol, lauryl alcohol, isotridecyl alcohol, myristyl alcohol, cetyl alcohol, cetearyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol and behenyl alcohol.

One particularly preferred alkyl polyalkylene glycol ether suitable for use in the anhydrous compositions of the present invention is a polyethylene glycol ether of cetyl alcohol conforming to the formula:

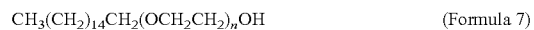

(Formula 7)

where n has an average value of from 2 to 20.

Another particularly preferred alkyl polyalkylene glycol ether suitable for use in the solid anhydrous composition of the present invention is a polyethylene glycol ether of cetearyl alcohol conforming to the formula:

(Formula 8)

where R is a blend of alkyl groups derived from cetyl and stearyl alcohols and n has an average value of from 2 to 20.

Yet another particularly preferred alkyl polyalkylene glycol ether suitable for use in the anhydrous compositions of the present invention is a polyethylene glycol ether of stearyl alcohol conforming to the formula:

(Formula 9)

where R is a blend of alkyl groups derived from cetyl and stearyl alcohols and n has an average value of from 2 to 20.

In an even more preferred embodiment, the solid anhydrous composition of the present invention is comprised of two non-ionic surfactants selected from the group consisting of polyethylene glycol ethers of cetyl, cetearyl and stearyl alcohols.

In an especially preferred embodiment, the solid anhydrous composition of the present invention is comprised of Steareth-2 and Steareth-20, two polyethylene glycol ethers of stearyl alcohol according to Formula 9, where n is 2 and 20, respectively.

Preferably, the non-ionic surfactant(s) is/are present at a concentration of from about 2% to about 12% by weight of the solid anhydrous composition.

In especially preferred embodiments comprising Steareth-2 and Steareth-20, Steareth-2 is present at concentrations of from about 0.5% to about 4.0% and Steareth-2 is present at concentrations of from about 2.0% to about 8.0%.

The solid anhydrous composition infused into the personal care article of the present invention further comprises at least one fatty alcohol, preferably at a concentration of from about 10% to about 50%. As used in the present application, by fatty alcohol is meant a primary alcohol, most often straight-chained, that has from eight to 20 carbon atoms. Fatty alcohols having from eight to 11 carbon atoms occur as oily liquids, while those having 12 or more are solids.

Preferred solid fatty alcohols suitable for use in the present invention are stearyl alcohol, cetearyl alcohol and cetyl alcohol.

A particularly preferred embodiment of the present invention is directed to solid anhydrous compositions having two solid fatty alcohols at a combined concentration of from about 55% to about 80% by weight of the solid anhydrous composition.

An especially preferred embodiment of the present invention is directed to anhydrous compositions having two solid fatty alcohols selected from the group consisting of stearyl alcohol, cetearyl alcohol and cetyl alcohol at a combined concentration of from about 55% to about 80% by weight of the solid anhydrous composition.

Other non-ionic surfactants suitable for use in the solid anhydrous compositions infused into the personal care articles of the present invention include alkanolamides, ethoxylated amides, esters, alkoxylated triglycerides, alkylpolyglucosides, amine oxides, sorbitan esters and ethoxylates as disclosed in O'Lenick, *Surfactants: Strategic Personal Care Ingredients* (Allured Publishing 2005 and McCutcheon's *Detergents and Emulsifiers* (1986).

Preferred anionic surfactants suitable for use in the invention of the present application include fatty alcohol sulfates, alpha olefin sulfonates, sarcosinates, and isethionates. Particularly preferred anionic surfactants are triethanolamine stearate, sodium cetearyl sulfate, triethanolamine stearyl sarconsinate and sodium cocoyl isethionate, typically at concentrations of from about 1% to about 5%.

The solid anhydrous composition infused into the personal care articles of the present invention also contain at least one cosmetically-acceptable oil, ester or liquid triglyceride. In addition to providing emolliency, the inclusion of one or more of these ingredients into the solid anhydrous composition serves to allow a formulator of skill in the art to adjust the melting point of the solid anhydrous composition to the desired temperature range for infusion (e.g., from about 45° C. to 55° C.)

A preferred liquid triglyceride is caprylic/capric triglyceride, a mixed triester of glycerin and caprylic and capric fatty acids derived from coconut & palm kernel oils.

Cosmetically-acceptable esters are well-known to those of skill in the art and include laurate, myristate, palmitate, oleate, stearate, isostearate, cocoate and benzoate esters.

In one aspect of the present invention, the solid anhydrous composition to be infused into personal care articles further comprises a solid cleansing agent.

In one embodiment of this aspect of the present invention, the personal care article is comprised of two sponge halves, where each half is infused with a different material (e.g., pourable soap, solid anhydrous composition containing a skincare active), and the two sponges are joined, bonded, adhered, fastened or otherwise affixed to each other. The two sponge halves may be affixed to each other by direct application of heat and/or pressure. Alternatively, an adhesive material may be applied to the first sponge half which is capable of reacting with the second sponge half upon application of either pressure or heat or both.

In a first embodiment of this aspect of the invention the solid cleansing agent is an alkanolamine salts of saturated fatty acids selected from the group consisting of lauric, myristic, palmitic and stearic acid.

A preferred embodiment of this aspect of the invention is directed to a personal care article in which the infused solid anhydrous composition comprises as the solid cleansing agent a triethanolamine soap of myristic acid, palmitic acid, stearic acid or mixtures thereof.

In a second embodiment of this aspect of the invention, the solid cleansing agent is a pourable soap. As will be appreciated by persons of skill in soap making technology, soaps are generally produced by combining fats and/or oils with a solution of caustic soda (sodium hydroxide or lye) or potash (potassium hydroxide) in a specific amount to cause saponification, the breakdown of the fats and/or oils into their component fatty acids and glycerin. Glycerin is then separated from the fatty acids, either by "salting out" or through a fat splitter, a device which employs water under high pressure and at a high temperature to produce free fatty acids in an oil phase and glycerin in a water phase. The resulting crude soap may be purified, for example, by boiling in water and re-precipitating the soap with salt. In this manner, remaining glycerin, sodium chloride and sodium hydroxide are removed. The crude soap is then dried and compacted into small, solid pellets having a moisture content of about 10% to 20%. These pellets, in turn, are processed into personal care products including soap bars.

"Pourable soaps" as claimed in the present application are different from "soaps" described in the preceding paragraph. Pourable soaps are produced from fats and oils without removal of the liberated glycerin. They are mixtures of crude soaps (with glycerin) to which additives, including additional glycerin, sugars, glycols, as well as small amounts of surfactants and/or alcohol(s) are added. These additional ingredients, in combination with the fatty acid salts, provide pourability and meltability as described below. Sample formulations for pourable soaps are disclosed in US Patent Application Publication No. 2006/0282966 at Paragraphs [0055]-[0061].

Pourable soaps according to the present invention are solid at temperatures of less than about 50° C. When heated to a temperature above about 50° C. (generally from about 50° C. to about 70° C.) pourable soaps melt and become liquid. When cooled below this melting point range, pourable soaps are reconstituted in solid form without having undergone significant changes in composition. In contrast, soaps as described above do not melt at elevated temperatures; instead, they decompose, char or burn. By the phrase "without having undergone significant changes in composition" is meant that, with the exception of a slight loss of water, the chemical composition of the pourable soap is essentially the same before and after melting/cooling.

Without being incorporated into a sponge-like material in the manner claimed in the present invention, pourable soaps produce essentially no foam in hard water when tested according to the foaming test method set out below. For purposes of this test, by "essentially no foam" is meant a foam height in a graduated cylinder of between 0 and 5 ml. By foam is meant a plurality of bubbles that form in or on the surface of a liquid.

As will be appreciated by persons of skill in the art "hard water" is water that has a specified mineral content, usually consisting of high levels of di- and tri-valent metal ions, mainly calcium and magnesium in the form of carbonates. Hard water may also include other metal ions (e.g. ferric), as well as other anions (e.g., chlorides and sulfates). The U.S. Department of the Interior (DOI), for example, has classified water hardness based on the grains per gallon concentration ("gpg") of minerals in water. Under the DOI scheme, water with 7.0 to 10.5 gpg mineral content (approximately, 120-180 ppm) is defined as hard. For purposes of the present application, "hard water" is defined as water having a concentration of di- or trivalent cationic salts of at least about 120 mg/L. For purposes of the foaming test described in the next paragraph, by "hard water" is meant water containing 200 ppm of a divalent salt (i.e., of Calcium or Magnesium).

Foaming test method: Prepare a 3% solution of the pourable soap to be tested by dissolving 3 grams of the soap in 97 ml of distilled water, using heat if necessary. Place 5 ml of the 3% soap solution into a 500 ml stoppered graduated cylinder.

Add about 100 ml of hard water. With a pipette add 1 ml olive oil (a simple substitute for synthetic sebum); then, without agitation, add hard water in a quantity sufficient to achieve a final cylinder volume of 250 ml. Gently invert the graduated cylinder 10 times within 25 seconds, let stand 5 seconds, and read the height of the foam. A pourable soap will produce essentially no foam. In contrast, when the above experiment is repeated with distilled water in place of hard water, the pourable soap produces a significantly measurable amount of foam. By "significantly measurable" is meant a foam height of at least 50 ml in a graduated cylinder.

Foam height and quality may also be measured and characterized by preparing a 3% solution of a pourable soap and measuring (in mm) the quantity of foam generated by 100 ml of the solution after mixing for one minute in a blender or similar mixing apparatus known to those of skill in the art.

Other methodologies for measuring foam, or lack thereof, produced by a pourable soap cleansing product are known to those of skill in the art and include the "Standard Test Method for Foaming Properties of Surface-Active Agents" published as ASTM D1173-53 (2001), otherwise known as the Ross-Miles Foam Test.

The quality of foam produced by a pourable soap incorporated into a sponge-like material as claimed in the present invention may also be measured by a consumer test panel.

Yet another aspect of the invention is directed to solid anhydrous cleanser compositions infused into a web of substantially water-insoluble fibers where the solid anhydrous composition has a melting point of from about 45° C. to about 55° C. and is comprised of (i) a mixture of at least two polyethylene glycol ethers of cetyl, cetearyl and/or stearyl alcohols, (ii) a mixture of at least two fatty alcohols selected from the group consisting of cetyl alcohol, cetearyl alcohol and stearyl alcohol, (iii) a liquid triglyceride and (iv) mineral oil.

A still further aspect of the invention is directed to solid anhydrous cleanser compositions infused into a web of substantially water-insoluble fibers where the solid anhydrous cleanser has a melting point of from about 45° C. to about 55° C. and is comprised of (i) a mixture of at least two polyethylene glycol ethers of cetyl, cetearyl and/or stearyl alcohols, (ii) a mixture of at least two fatty alcohols selected from the group consisting of cetyl alcohol, cetearyl alcohol and stearyl alcohol, (iii) a liquid triglyceride and (iv) mineral oil. In a preferred embodiment of this aspect of the invention, the liquid triglyceride is caprylic/capric triglyceride.

Yet another aspect of the invention is directed to solid anhydrous cleanser compositions infused into a web of substantially water-insoluble fibers where the solid anhydrous cleanser has a melting point of from about 45° C. to about 55° C. and is comprised of (i) a cosmetically-acceptable ester that is solid at room temperature, (ii) a liquid triglyceride and (iii) mineral oil. In a preferred embodiment of this aspect of the invention, the cosmetically-acceptable ester that is solid at room temperature is isononyl isononanoate and the liquid triglyceride is caprylic/capric triglyceride.

A further aspect of the present invention is directed to solid anhydrous sunscreen compositions infused into a web of substantially water-insoluble fibers where the solid anhydrous sunscreen composition has a melting point of from 45° C. to 60° C. and is comprised of (i) a cosmetically-acceptable ester, (ii) at least one gelling agent and (iii) a combination of at least two organic sunscreens.

In a preferred embodiment of this aspect of the invention, the at least one gelling agent is siliconyl polyethylene.

In a preferred embodiment of this aspect of the invention, the solid anhydrous sunscreen composition having a melting point of from 45° C. to 60° C. is comprised of (i) at least one gelling agent, (ii) a combination of at least two organic sunscreens and (iii) an agent that inhibits the crystallization of the organic sunscreens. A preferred agent that inhibits the crystallization of organic sunscreens is hydroxy polyester available as Hydroxy Polyester K-82P from Koster Keunen.

Skincare and Haircare Actives

Numerous skincare and haircare actives—both personal care (cosmetic and OTC) and dermatologic (i.e., medicated Rx) products—that are suitable for topical application may be added to the solid anhydrous compositions of the present invention and thereby infused into and delivered from the personal care articles of the present invention.

One aspect of the present invention is directed to delivery of skincare actives which help to improve retention of moisture on the skin and/or skin elasticity, reduce transepidermal water loss including, but not limited to, emollients, humectants (polyols), and occlusive conditioning agents (petrolatum and dimethicone). Capric/caprylic triglycerides are one preferred emollient.

Another aspect of the present invention is directed to delivery to the skin of skincare actives which help to reduce the appearance of and/or prevent the formation of fine lines, wrinkles and other conditions associated with biological or environmentally-induced aging, including, but not limited to, topical anti-inflammatory agents, antioxidants, vitamins and derivatives thereof, skin soothing agents and skin bleaching/lightening agents.

Yet another aspect of the present invention is directed to delivery to the skin of self-tanning agents (e.g., dihydroxyacetone).

Still another aspect of the present invention is directed to delivery of sunscreens or physical sunblocks to the skin. The following sunscreens and sunblocks may be used in anhydrous compositions of the present invention: p-Aminobenzoic acid up to 15%; Avobenzone up to 3%; Cinoxate up to 3%; Dioxybenzone up to 3%; Homosalate up to 15%; Menthyl anthranilate up to 5%; Octocrylene up to 10%; Octylmethoxycinnamate (Octinoxate) up to 7.5%; Octyl salicylate up to 5%; Oxybenzone up to 6%; Padimate O up to 8%; Phenylbenzimidazole sulfonic acid (Ensulizole) up to 4%; Sulisobenzone up to 10%; Titanium dioxide up to 25%; Trolamine salicylate up to 12%; Zinc oxide up to 25%. The above-listed sunscreens and use concentrations are approved by the US Food and Drug Administration at the time of filing of this application. Other sunscreens and sunblocks, including those under review by the FDA or its counterpart agencies in other countries and/or approved in countries outside the US are also suitable for inclusion in anhydrous compositions of the present invention.

Additional examples of skincare actives and haircare actives that may be added to the solid anhydrous compositions infused into the personal care articles of the present invention are listed in the International Cosmetic Ingredient Dictionary and Handbook, (11$^{th}$ Edition), published by the Cosmetic Fragrance and Toiletry Association, as well as U.S. Pat. Nos. 6,492,326 and 6,277,892, 6,974,799, and U.S. Patent Application Publication Nos. 2005/0142095 and 2004/0180020.

Preservative System

The solid anhydrous compositions infused into and delivered from the personal care articles of the present invention optionally contain one or more preservatives (i.e., antimicrobial agents) well-known to those of skill in the art and disclosed, for example, in David C. Steinberg, *Preservatives for Cosmetics* (Allured Publishing, 2006).

One preservative system suitable for use in the solid anhydrous composition of the present invention is a combination of parabens (isopropylparaben, isobutylparaben and butylparaben) and phenoxyethanol, which is commercially-available under the tradename Liquipar PE from ISP (Wayne, N.J.).

Another suitable preservative is Arlasilk Phospholipid PTC a phospholipid complex composed predominantly of diester phosphatides with multiple long chain groups conforming to the structure:

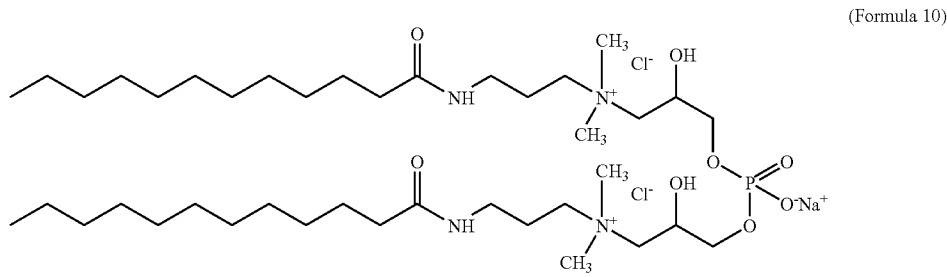

(Formula 10)

EXAMPLES

The following examples are further illustrative of the present invention. The components and specific ingredients are presented as being typical, and various modifications can be derived in view of the foregoing disclosure within the scope of the invention.

Example 1

Solid Anhydrous Emollient Composition

| | | |
|---|---|---|
| Behentrimonium Methosulfate (and) Cetearyl Alcohol (Incroquat TMS-50) | 10.0 | 3.0-12.0 |
| Steareth-2 | 2.0 | 0.5-3.0 |
| Steareth-20 | 5.0 | 2.0-8.0 |
| Stearyl Alcohol 95% | 20.0 | 12.0-35.0 |
| Cetyl Alcohol 95% | 40.5 | 25.0-45.0 |
| Petrolatum | 5.0 | 3.0-10.0 |
| Capric/Caprylic Triglycerides | 16.5 | 12.0-25.0 |
| Phenoxyethanol (and) Isopropylparaben (and) Isobutylparaben (and) Butylparaben | 1.0 | 1.0 |

At about 65° C., melt and mix with gentle agitation until homogenous the fatty alcohols (cetyl and stearyl), the non-ionic surfactants (Steareth-2 and Steareth-20), the occlusive conditioning agent (petrolatum) and the liquid triglyceride (caprylic/capric triglycerides). Add cationic quaternary surfactant (Incroquat TMS). Add preservatives (phenoxyethanol+parabens). Allow to cool and solidify.

Example 2

Solid Anhydrous Emollient Composition

| | | |
|---|---|---|
| Distearyldimonium chloride (Varisoft TA 100) | 10.0 | 3.0-12.0 |
| Steareth-2 | 2.0 | 0.5-3.0 |
| Steareth-20 | 5.0 | 2.0-8.0 |
| Stearyl Alcohol 95% | 20.0 | 12.0-35.0 |
| Cetyl Alcohol 95% | 38.0 | 25.0-45.0 |
| Petrolatum | 5.0 | 3.0-10.0 |
| Capric/Caprylic Triglycerides | 19.0 | 12.0-25.0 |
| Phenoxyethanol (and) Isopropylparaben (and) Isobutylparaben (and) Butylparaben | 1.0 | 1.0 |

Same procedure as in Example 1, substituting Varisoft TA 100 for Incroquat TMS.

Example 3

Solid Anhydrous Emollient Composition

Multilamellar Liquid Crystal Emulsifier

| | | |
|---|---|---|
| Behentrimonium Methosulfate (and) Cetearyl Alcohol (Incroquat TMS-50) | 10.0 | 3.0-12.0 |
| Cetearyl Alcohol (and) Sucrose Distearate (and) Sucrose Monostearate (Crystalcast) | 10.0 | 3.0-12.0 |
| Stearyl Alcohol 95% | 20.0 | 12.0-35.0 |
| Cetyl Alcohol 95% | 36.0 | 25.0-45.0 |
| Petrolatum | 5.0 | 3.0-10.0 |
| Capric/Caprylic Triglycerides | 18.0 | 12.0-25.0 |
| Phenoxyethanol (and) Isopropylparaben (and) Isobutylparaben (and) Butylparaben | 1.0 | 1.0 |

Same procedure as in Example 1, adding Crystalcast after Incroquat TMS.

Example 4

Solid Anhydrous Emollient Composition

Multilamellar Liquid Crystal Emulsifier

| | | |
|---|---|---|
| Behentrimonium Methosulfate (and) Cetearyl Alcohol (Incroquat TMS-50) | 10.0 | 3.0-12.0 |
| Cetearyl Glucoside (and) Cetearyl Alcohol (Emulgade 6850) | 10.0 | 3.0-15.0 |
| Stearyl Alcohol 95% | 20.0 | 12.0-35.0 |
| Cetyl Alcohol 95% | 36.0 | 25.0-45.0 |
| Petrolatum | 5.0 | 3.0-10.0 |
| Capric/Caprylic Triglycerides | 18.0 | 12.0-25.0 |
| Phenoxyethanol (and) Isopropylparaben (and) Isobutylparaben (and) Butylparaben | 1.0 | 1.0 |

Same procedure as in Example 1, adding Crystalcast after Incroquat TMS.

Example 5

Solid Anhydrous Emollient Composition

| | | |
|---|---|---|
| Steapyrium Chloride | 2.0 | 0.5-4.0 |
| Steareth-2 | 2.0 | 0.5-3.0 |
| Steareth-20 | 5.0 | 2.0-8.0 |
| Stearyl Alcohol 95% | 25.0 | 12.0-35.0 |
| Cetyl Alcohol 95% | 42.0 | 25.0-45.0 |
| Petrolatum | 5.0 | 3.0-10.0 |
| Capric/Caprylic Triglycerides | 18.0 | 12.0-25.0 |
| Phenoxyethanol (and) Isopropylparaben (and) Isobutylparaben (and) Butylparaben | 1.0 | 1.0 |

Same procedure as in Example 1, substituting Steapyrium Chloride for Incroquat TMS.

Example 6

Solid Anhydrous Sunscreen Composition

| | | |
|---|---|---|
| Behentrimonium Methosulfate (and) Cetearyl Alcohol | 10.00 | 3.0-12.0 |
| Steareth-2 | 2.0 | 0.5-3.0 |
| Steareth-20 | 5.0 | 2.0-8.0 |
| Stearyl Alcohol 95% | 20.0 | 12.0-35.0 |
| Cetyl Alcohol 95% | 40.5 | 25.0-45.0 |
| Micronized Titanium Dioxide (Kobo GCP50 NTTS) | 21.5 | 10.0-25.0 |
| Phenoxyethanol (and) Isopropylparaben (and) Isobutylparaben (and) Butylparaben | 1.0 | 1.0 |

Same procedure as in Example 1, adding inorganic sunscreens before preservatives.

Example 7

Solid Anhydrous Sunscreen Composition

| | | |
|---|---|---|
| Behentrimonium Methosulfate (and) Cetearyl Alcohol (Incroquat TMS-50) | 10.0 | 3.0-12.0 |
| Steareth-2 | 2.0 | 0.5-3.0 |
| Steareth-20 | 5.0 | 2.0-8.0 |
| Stearyl Alcohol 95% | 35.0 | 12.0-35.0 |
| Cetyl Alcohol 95% | 21.5 | 25.0-45.0 |
| Oxybenzone | 2.50 | 1.0-6.0 |
| Avobenzone | 3.00 | 1.0-3.0 |
| Homosalate | 10.00 | 3.0-15.0 |
| Octisalate | 5.00 | 2.0-5.0 |
| Octocrylene | 5.00 | 2.0-10.0 |
| Phenoxyethanol (and) Isopropylparaben (and) Isobutylparaben (and) Butylparaben | 1.00 | 1.0-2.5 |

Same initial procedure as in Example 1. In a separate vessel, at a temperature of about 70° C., mix homosalate, octisalate and octocrylene. To this mixture of sunscreens, add oxybenzone; melt and mix. Then, add avobenzone; melt and mix. Combine mixture of quaternary surfactant+nonionic surfactants+fatty alcohol mixtures with sunscreen mixture. Allow to cool.

Example 8

Solid Anhydrous Autobronzer Composition

| | | |
|---|---|---|
| Behentrimonium Methosulfate (and) Cetearyl Alcohol (Incroquat TMS-50) | 10.0 | 3.0-12.0 |
| Steareth-2 | 2.0 | 0.5-3.0 |
| Steareth-20 | 5.0 | 2.0-8.0 |
| Stearyl Alcohol 95% | 14.0 | 12.0-35.0 |
| Cetyl Alcohol 95% | 35.0 | 25.0-45.0 |
| Dihydroxyacetone | 8.0 | 6.0-9.0 |
| Glycerin | 5.0 | 3.0-8.0 |
| $C_{12}$-$C_{15}$ Alkyl Benzoate (Finsolv TN) | 20.0 | 15.0-25.0 |
| Phenoxyethanol (and) Isopropylparaben (and) Isobutylparaben (and) Butylparaben | 1.0 | 1.0-2.5 |

In a main vessel at a temperature of about 65° C., mix the quaternary and nonionic surfactants and ester (Finsolv TN) until homogenous. Allow main vessel to cool to a temperature of about 45° C. In a separate vessel, at a temperature of about 40° C.-45° C., disperse DHA in glycerin. Combine DHA dispersion in main vessel hold at about 45° C. Add preservative. Mix until homogenous. Allow to cool and solidify.

Example 9

Solid Anhydrous Skin Cleanser Composition

Anionic/Nonionic Emulsifiers

| | | |
|---|---|---|
| Stearic Acid | 4.2 | 2.0-6.0 |
| Triethanolamine 99% | 1.8 | 1.0-3.0 |
| Steareth-2 | 2.0 | 0.5-5.0 |
| Steareth-20 | 5.0 | 2.0-10.0 |
| Stearyl Alcohol 95% | 20.0 | 12.0-35.0 |
| Cetyl Alcohol 95% | 34.0 | 25.0-45.0 |
| Petrolatum | 5.0 | 3.0-10.0 |
| Capric/Caprylic Triglycerides | 18.0 | 12.0-25.0 |
| Mineral Oil | 9.0 | 5.0-20.0 |
| Phenoxyethanol (and) Isopropylparaben (and) Isobutylparaben (and) Butylparaben | 1.0 | 1.0 |

Melt and mix all ingredients until homogenous at a temperature of about 65° C. Allow to cool and solidify.

Example 10

Solid Anhydrous Skin Cleanser Composition

Nonionic Emulsifiers

| | | |
|---|---|---|
| Steareth-2 | 3.0 | 0.5-5.0 |
| Steareth-20 | 8.0 | 2.0-10.0 |
| Stearyl Alcohol 95% | 20.0 | 12.0-35.0 |
| Cetyl Alcohol 95% | 36.0 | 25.0-45.0 |
| Petrolatum | 5.0 | 3.0-10.0 |
| Capric/Caprylic Triglycerides | 18.0 | 12.0-25.0 |

-continued

| | | |
|---|---|---|
| Mineral Oil | 9.0 | 5.0-20.0 |
| Phenoxyethanol (and) Isopropylparaben (and) Isobutylparaben (and) Butylparaben | 1.0 | 1.0 |

Melt and mix all ingredients until homogenous at a temperature of about 65° C. Allow to cool and solidify.

Example 11

Sunscreen Ester Anhydrous Solid Composition

| | | | | |
|---|---|---|---|---|
| Part A | Hydroxy Polyester K-82P | 8.5 | 7.0-10.0 |
| | Behenyl Alcohol S-75 | 4.8 | 4.0-7.0 |
| | Siliconyl Polyethylene | 9.5 | 6.0-10.0 |
| | Isononyl Isononanoate | 37.4 | 30.0-40.0 |
| | Phenyl Trimethicone (Dow Corning Cosmetic Grade Fluid 556) | 4.8 | 3.0-6.0 |
| Part B | Avobenzone | 2.0 | 1.0-3.0 |
| | Homosalate | 15.0 | 5.0-15.0 |
| | Octyl Salicylate | 5.0 | 2.0-5.0 |
| | Octinoxate | 7.5 | 3.0-7.5 |
| | Octocrylene | 2.5 | 1.0-2.5 |
| | Benzophenone-3 | 3.0 | 1.0-6.0 |

Mix and melt Part A ingredients at about 65° C. Mix Part B sunscreen ingredients as in Example 7. Combine Parts A and B. Allow to cool and solidify.

Example 12

Anhydrous Solid Ester/Mineral Oil Composition

| | | |
|---|---|---|
| Hydroxy Polyester K-82P | 8.5 | 7.0-10.0 |
| Behenyl Alcohol S-75 | 4.8 | 4.0-7.0 |
| Siliconyl Polyethylene | 9.5 | 6.0-10.0 |
| Isononyl Isononanoate | 37.4 | 30.0-40.0 |
| Phenyl Trimethicone (Dow Corning Cosmetic Grade Fluid 556 | 4.8 | 3.0-6.0 |
| Capric/Caprylic Triglyceride | 20.0 | 15.0-30.0 |
| Mineral Oil | 15.0 | 5.0-25.0 |

Melt and mix all ingredients at 65° C. Allow to cool and solidify.

Examples

Infusion Manufacturing

As will be recognized by persons of skill in the art, a variety of different processes and equipment can be used to infuse the solid anhydrous compositions of the present invention into a web of substantially water-insoluble fibers (e.g., sponge pad). As used in the present invention, by the terms "infuse" and "infusion" are meant dipping/soaking, spraying, injection, misting, and similar processes known in the art. For purposes of the following examples, the web of substantially water-insoluble fibers is referred to as a sponge.

In one embodiment, the solid anhydrous composition is heated to a temperature of from about 40° C. to about 80° C., preferably from about 40° C. to 45° C. to about 70° C. and maintained at temperature in molten (i.e., pourable) form in a kettle or similar vessel by electric or gas burning heating elements. Alternatively, the solid anhydrous composition can be heated into molten form elsewhere and transferred to the vessel via a pipe. One or more sponges are placed in the basket, which may be slotted, and lowered into the molten anhydrous composition, such that the sponges are submerged in and allowed to absorb the anhydrous composition.

The duration of submerging the sponges (i.e., immersion time) can be varied to control the amount of molten anhydrous composition absorbed by the sponges. Immersion time can range from about 5 to 50 seconds and, in a preferred embodiment, is preferably less than 10 seconds. As will be readily-understood by those of skill in the art, a shorter immersion time may be used when it is desired to essentially coat only the exterior of the sponges, while longer periods of time may be used to allow coating of the interior fibers of the sponges. Other factors that can be used to control the degree (i.e., amount) of coating of the fibers in the sponges include varying the viscosity of the molten anhydrous composition, the degree of porosity and pore size of the sponges, the material(s) of the sponges, etc.

Preferably, the sponges are compressed prior to being immersed into the molten anhydrous composition. Rates of compression may be adjusted to take into account differences in sponge materials. In one embodiment, sponges are compressed between upper and lower squeezing plates in the basket. As pressure is slowly released (e.g., by separating the two plates), the sponges absorb the molten anhydrous composition. The sponges may be compressed several times during the immersion process to remove excess air. Application of specified amounts of pressure to the sponges via the plates allows measured absorption of the molten anhydrous composition by the sponges.

After dipping, the basket is raised to take the soaked sponges out of the molten anhydrous composition. In one embodiment, excess molten anhydrous composition is to allowed to drip off the sponge. In another embodiment, the sponges are squeezed to extract excess soap. The duration and number of times the sponges are squeezed will vary based on the nature of the sponge materials and its properties (porosity, density, etc.). The squeezed sponges are then transferred to a drying/cooling area during which time the molten anhydrous composition resolidifies. In one embodiment, the cooling/drying step takes place at room temperature without forced drying to remove excess water. Alternatively, an induced artificial cooling and/or forced air drying step may be utilized.

In other embodiments, the sponges are infused by injection or spraying. In the former method, a plurality of injectors (e.g., hollow needles) are inserted into the sponges. Molten anhydrous composition is pumped into the sponges through the injectors. Injection depth, pump output/speed, and pump temperature can be varied to control the amount of molten anhydrous composition infused into the sponge. In the latter method, molten anhydrous composition is sprayed through a plurality of spray nozzles. The volume, viscosity and temperature of sprayed molten anhydrous composition, as well as spray pressure and the material of the sponges are among parameters that can be adjusted to control amount of molten anhydrous composition that is absorbed by the sponges.

The methods and apparatus for infusing a molten cleansing agent into sponges as set out in Paragraphs [0069]-[0117] of US Patent Application Publication No. 2006/0282966 as well as the accompanying FIGS. 1-21 referenced in those paragraphs are equally applicable to and may be used for infusion of the anhydrous compositions of the present invention into sponges. Infusion of anhydrous compositions of the present invention into sponges is typically carried out at temperatures of from about 40° C.-45° C. (for autobronzer) to about 75° C.-80° C.

Another aspect of the present invention is directed to applying a solid anhydrous composition infused into a web of substantially water-insoluble fibers to a wet or moistened hard surface in an industrial, commercial, hospital or household environment where the solid anhydrous composition has a melting point of from about 45° C. to about 55° C. and is comprised of (a) at least one surfactant selected from the group consisting of cationic quaternary surfactants, anionic surfactants and non-ionic surfactants or at least one multilamellar liquid crystal emulsifier system, (b) at least one fatty alcohol, preferably two, (c) at least one emollient selected from the group consisting of cosmetically-acceptable oils, esters and liquid triglycerides, (d) at least one active ingredient and (e) optionally, a solid cleansing agent having a melting point from about 50° C. to about 70° C.

In one embodiment of this aspect of the present invention, the wet or moistened hard surface is wood, ceramic or porcelain tile, natural or synthetic stone, plastic or metal.

In another embodiment of this aspect of the present invention, the at least one active ingredient is a moisturizer or conditioning agent; a material that absorbs, attenuates or blocks ultraviolet radiation ("uv protectants"); an antimicrobial agent; a hard surface disinfectant or sanitizing agent; or an antioxidant.

A still further aspect of the present invention is directed to applying a solid anhydrous composition infused into a web of substantially water-insoluble fibers to a wet or moistened natural or synthetic leather where the solid anhydrous composition has a melting point of from about 45° C. to about 55° C. and is comprised of (a) at least one surfactant selected from the group consisting of cationic quaternary surfactants, anionic surfactants and non-ionic surfactants or at least one multilamellar liquid crystal emulsifier system, (b) at least one fatty alcohol, preferably two, (c) at least one emollient selected from the group consisting of cosmetically-acceptable oils, esters and liquid triglycerides, (d) at least one active ingredient selected from the group consisting of conditioners, moisturizing agents, preservatives, antioxidants, and uv protectants and (e) optionally, a solid cleansing agent having a melting point from about 50° C. to about 70° C.

Yet another aspect of the present invention is directed to applying a solid anhydrous composition infused into a web of substantially water-insoluble fibers to a wet or moistened exterior surface of an automotive or marine vehicle where the solid anhydrous composition has a melting point of from about 45° C. to about 55° C. and is comprised of (a) at least one surfactant selected from the group consisting of cationic quaternary surfactants, anionic surfactants and non-ionic surfactants or at least one multilamellar liquid crystal emulsifier system, (b) at least one fatty alcohol, preferably two, (c) at least one emollient selected from the group consisting of cosmetically-acceptable oils, esters and liquid triglycerides, (d) at least one active ingredient selected from the group consisting of conditioners, moisturizing agents, preservatives, antioxidants, and uv protectants and (e) optionally, a solid cleansing agent having a melting point from about 50° C. to about 70° C.

Still another aspect of the present invention is directed to applying a solid anhydrous composition infused into a web of substantially water-insoluble fibers to a wet or moistened piece of recreational sports equipment where the solid anhydrous composition has a melting point of from about 45° C. to about 55° C. and is comprised of (a) at least one surfactant selected from the group consisting of cationic quaternary surfactants, anionic surfactants and non-ionic surfactants or at least one multilamellar liquid crystal emulsifier system, (b) at least one fatty alcohol, preferably two, (c) at least one emollient selected from the group consisting of cosmetically-acceptable oils, esters and liquid triglycerides, (d) at least one active ingredient selected from the group consisting of conditioners, moisturizing agents, preservatives, antioxidants, and uv protectants and (e) optionally, a solid cleansing agent having a melting point from about 50° C. to about 70° C. Non-limiting examples of recreational sports equipment are skis, surfboards and snowboards.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A method for delivering a cleansing agent and at least one active ingredient to a wet substrate selected from the group of wet skin or wet hair comprising contacting the wet substrate with a personal care article made of a flexible, three-dimensional, water-absorbent substrate material comprised of a web of substantially water-insoluble fibers, 1 where the personal care article is comprised of two halves, wherein
    (a) a first half is infused with a solid anhydrous composition having a melting point of from about 45° C. to about 55° C. said anhydrous composition comprising (i) at least one cationic quaternary surfactant (ii) at least one fatty alcohol, (iii) at least one emollient selected from the group consisting of cosmetically-acceptable oils, esters and liquid triglycerides, and (iv) at least one active ingredient and
    (b) a second half is infused with a solid cleansing agent that is a pourable soap having a melting point from about 50° C. to about 70° C. and is impregnated substantially throughout the interior of the flexible, three-dimensional, water-absorbent substrate, where the second half produces lather in both hard as well as soft water
    wherein the first and second halves are joined, bonded, adhered, fastened or otherwise affixed to each other and further wherein the personal care article can be used multiple times.

2. The method of claim 1 where the cationic quaternary surfactant is selected from the group consisting of alkyl quats, alylamido quats, imidazoline quats and polymeric quats.

3. The method of claim 2 where the cationic quaternary surfactant is selected from the group consisting of behentrimonium methosulfate, distearyldimonium chloride, steapyrium chloride, lauramidopropyl PG-dimonium chloride phosphate and cocamidopropyl PG-dimonium chloride phosphate.

4. The method of claim 1 where the at least one fatty alcohol is a solid fatty alcohol.

5. The method of claim 4 where the at least one fatty alcohol is two solid fatty alcohols selected from the group consisting of cetyl alcohol, cetearyl alcohol and stearyl alcohol where the two solid fatty alcohols are present at a combined concentration of from about 55% to about 80% by weight of the solid anhydrous composition.

6. The method of claim 1 where the active ingredient is a skincare active or haircare active selected from the group consisting of emollients, humectants, occlusive conditioning agents, sunscreens or physical sunblocks, self-tanning agents, anti-inflammatory agents, antioxidants, vitamins and derivatives thereof, skin soothing agents and skin bleaching/lightening agents.

7. The method of claim 6 where the solid anhydrous composition further comprises an occlusive conditioning agent.

8. The method of claim 7 where the occlusive conditioning agent is petrolatum.

9. The method of claim 6 where the skincare active is a self-tanning agent and the solid anhydrous composition containing the self-tanning agent has a melting point of from 40 to 45° C.

10. The method of claim 1 where the at least one emollient is a liquid triglyceride.

11. The method of claim 10 where the at least one emollient is caprylic/capric triglycerides.

\* \* \* \* \*